US010271793B2

(12) United States Patent
Vanney et al.

(10) Patent No.: US 10,271,793 B2
(45) Date of Patent: Apr. 30, 2019

(54) MEDICAL DEVICE GUIDEWIRE WITH HELICAL CUTOUT AND COATING

(71) Applicant: St. Jude Medical, Atrial Fibrillation Division, Inc., St. Paul, MN (US)

(72) Inventors: Guy P. Vanney, Blaine, MN (US); Pär Gustafsson, Uppsala (SE)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 68 days.

(21) Appl. No.: 15/158,503

(22) Filed: May 18, 2016

(65) Prior Publication Data

US 2016/0310079 A1 Oct. 27, 2016

Related U.S. Application Data

(63) Continuation of application No. 13/465,866, filed on May 7, 2012, now Pat. No. 9,364,640.

(51) Int. Cl.
*A61B 5/05* (2006.01)
*A61B 5/00* (2006.01)
(Continued)

(52) U.S. Cl.
CPC .......... *A61B 5/6851* (2013.01); *A61B 5/0245* (2013.01); *A61B 5/062* (2013.01);
(Continued)

(58) Field of Classification Search
None
See application file for complete search history.

(56) References Cited

U.S. PATENT DOCUMENTS 4,961,433 A * 10/1990 Christian ............... H01R 13/33
600/434
5,386,828 A * 2/1995 Owens ..................... A61B 5/06
600/13
(Continued)

FOREIGN PATENT DOCUMENTS

CN 1225282 A 8/1999
CN 201668548 U 12/2010
(Continued)

OTHER PUBLICATIONS

State Intellectual Property Office, Search Report, dated Mar. 9, 2016. pp. 2, China.
(Continued)

*Primary Examiner* — Joel F Brutus
(74) *Attorney, Agent, or Firm* — Dykema Gossett PLLC

(57) ABSTRACT

A guidewire for a medical device is disclosed. The guidewire includes an elongate body, a proximal connector assembly, a corewire, and a sensor assembly. The body has an annular wall that defines an interior lumen. The proximal connector assembly is coupled to the body and is configured for connection to a medical positioning system. The corewire extends through the lumen. The sensor assembly located on a distal end of the corewire is electrically connected to the proximal connector assembly. The sensor assembly is configured to generate an electrical signal indicative of a position of the sensor assembly in a reference coordinate system defined by the medical positioning system. The body includes a helical cutout extending over a predetermined length of the body. The helical cutout is configured to increase the flexibility of the body over the predetermined length of the body.

8 Claims, 8 Drawing Sheets

(51) Int. Cl.
*A61M 25/09* (2006.01)
*A61B 5/06* (2006.01)
*A61B 5/0245* (2006.01)
*A61M 25/00* (2006.01)
*A61B 34/20* (2016.01)

(52) U.S. Cl.
CPC .............. *A61B 5/066* (2013.01); *A61B 34/20* (2016.02); *A61M 25/09* (2013.01); *A61B 2034/2051* (2016.02); *A61B 2562/0223* (2013.01); *A61B 2562/12* (2013.01); *A61M 2025/0002* (2013.01); *A61M 2025/0915* (2013.01); *A61M 2025/09083* (2013.01); *A61M 2025/09091* (2013.01); *A61M 2025/09133* (2013.01); *A61M 2025/09175* (2013.01); *A61M 2025/09183* (2013.01)

(56) References Cited

U.S. PATENT DOCUMENTS

| | | |
|---|---|---|
| 5,409,015 A | 4/1995 | Palermo |
| 5,769,796 A | 6/1998 | Palermo et al. |
| 6,233,476 B1 | 5/2001 | Strommer et al. |
| 6,498,944 B1 | 12/2002 | Ben-Haim et al. |
| 6,565,514 B2 | 5/2003 | Svanerudh et al. |
| 6,788,967 B2 | 9/2004 | Ben-Haim et al. |
| 7,197,354 B2 | 3/2007 | Sobe |
| 7,386,339 B2 | 6/2008 | Strommer et al. |
| 7,645,233 B2 | 1/2010 | Tulkki et al. |
| 7,724,148 B2 | 5/2010 | Samuelsson et al. |
| 7,775,988 B2 | 8/2010 | Pijls |
| 7,931,603 B2 | 4/2011 | von Malmborg et al. |
| 8,038,628 B2 | 10/2011 | von Malmborg et al. |
| 8,109,889 B2 | 2/2012 | von Malmborg et al. |
| 2002/0139785 A1* | 10/2002 | Peacock, III ..... A61M 25/0052 219/121.72 |
| 2003/0220588 A1* | 11/2003 | Tenerz ................. A61M 25/09 600/585 |
| 2004/0097804 A1 | 5/2004 | Sobe |
| 2004/0181174 A2 | 9/2004 | Davis et al. |
| 2005/0107688 A1 | 5/2005 | Strommer |
| 2005/0197557 A1 | 9/2005 | Strommer et al. |
| 2006/0041270 A1 | 2/2006 | Lenker et al. |
| 2006/0052750 A1* | 3/2006 | Lenker ................ A61B 17/3439 604/164.01 |
| 2007/0299424 A1 | 12/2007 | Cumming et al. |
| 2008/0027561 A1 | 1/2008 | Mitelberg et al. |
| 2008/0132806 A1 | 6/2008 | Smith |
| 2008/0255446 A1 | 10/2008 | Akins |
| 2008/0255475 A1 | 10/2008 | Kondrosky et al. |
| 2009/0112128 A1* | 4/2009 | Schiff .................... A61B 5/061 600/585 |
| 2009/0192412 A1 | 7/2009 | Sela et al. |
| 2009/0192413 A1* | 7/2009 | Sela ......................... A61B 5/06 600/585 |
| 2010/0191151 A1* | 7/2010 | Kwak ................ A61B 18/1492 600/585 |
| 2011/0152721 A1 | 6/2011 | Sela |

FOREIGN PATENT DOCUMENTS

| | | |
|---|---|---|
| EP | 0367472 A2 | 5/1990 |
| EP | 0925803 A2 | 6/1999 |
| EP | 2085108 A2 | 5/2009 |
| JP | 2014-42645 A | 3/2014 |
| WO | 9913532 A2 | 3/1999 |
| WO | 2000/038775 A2 | 7/2000 |
| WO | 2012061935 A1 | 5/2012 |

OTHER PUBLICATIONS

State Intellectual Property Office, First Office Action, dated Mar. 23, 2016. pp. 5, China.

* cited by examiner

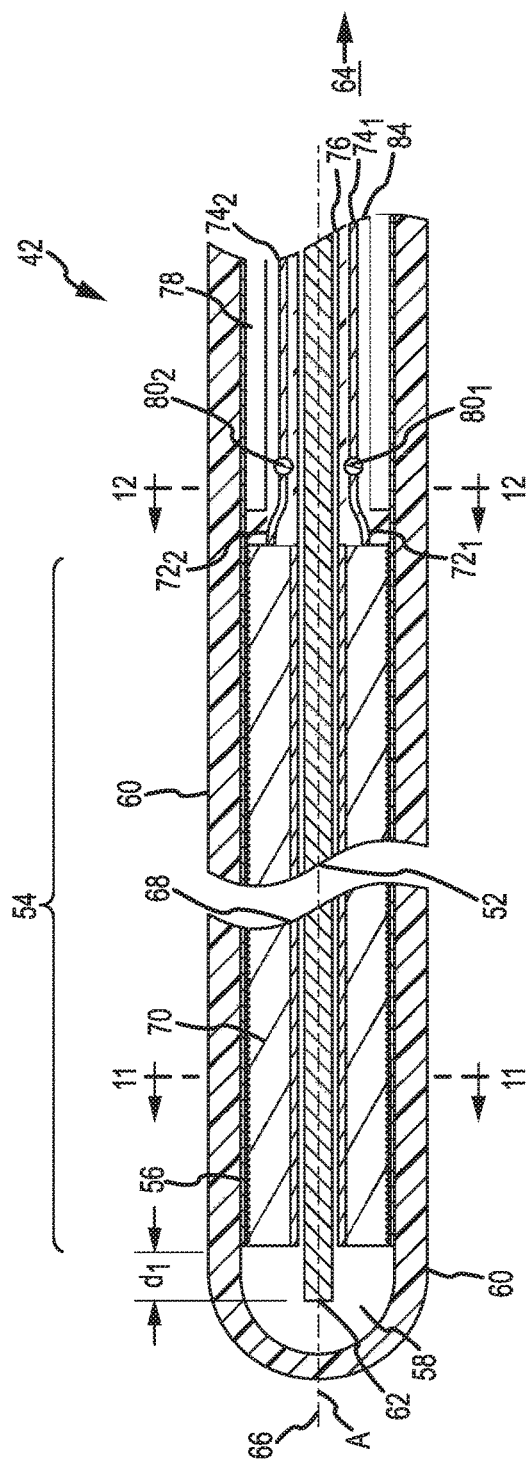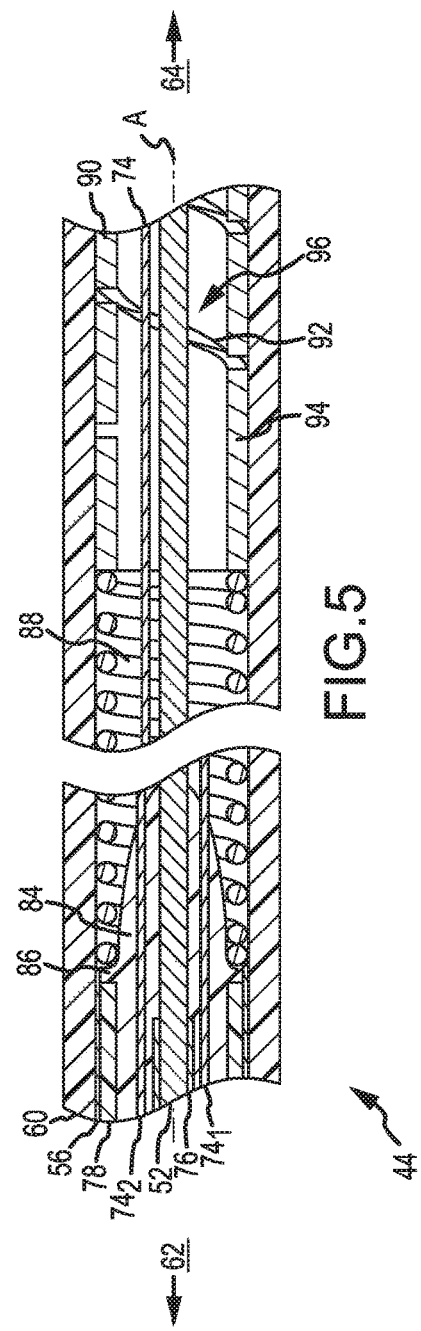

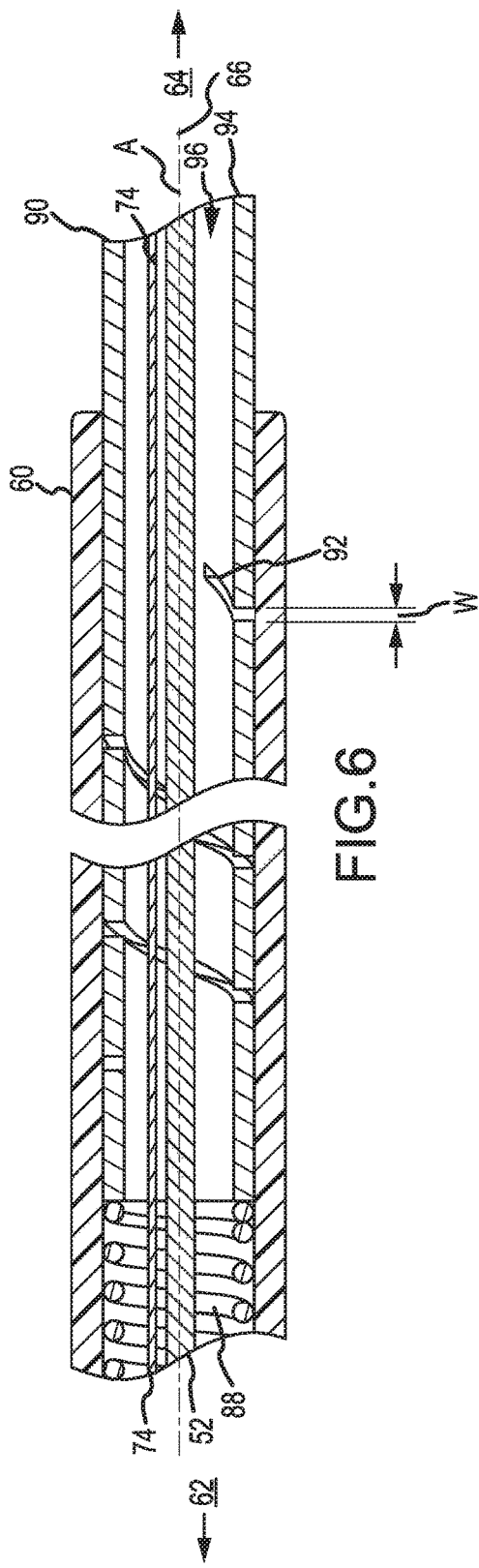
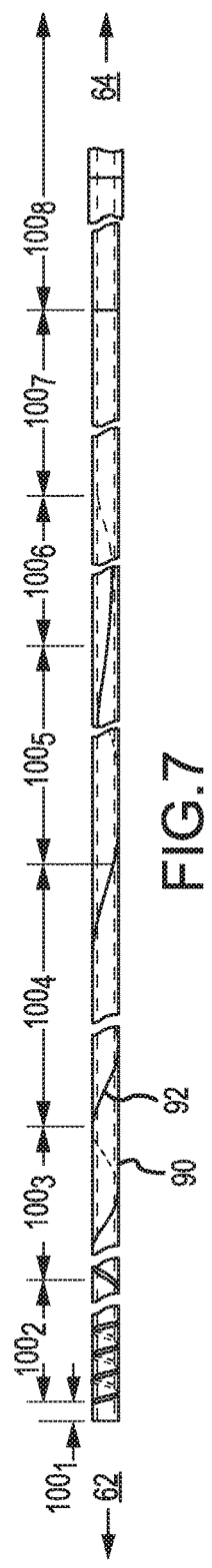

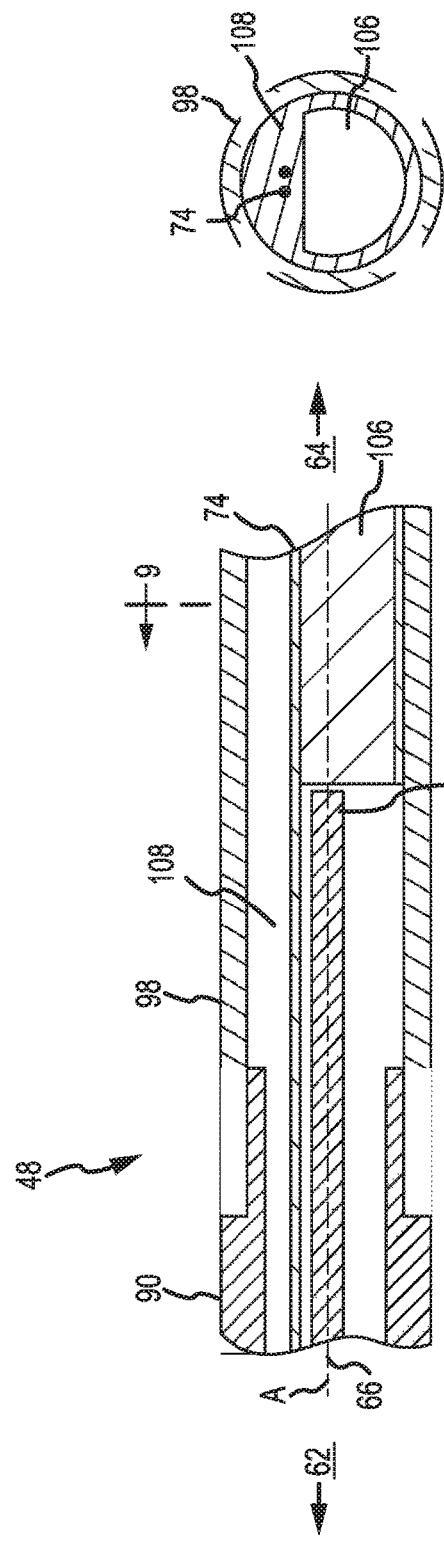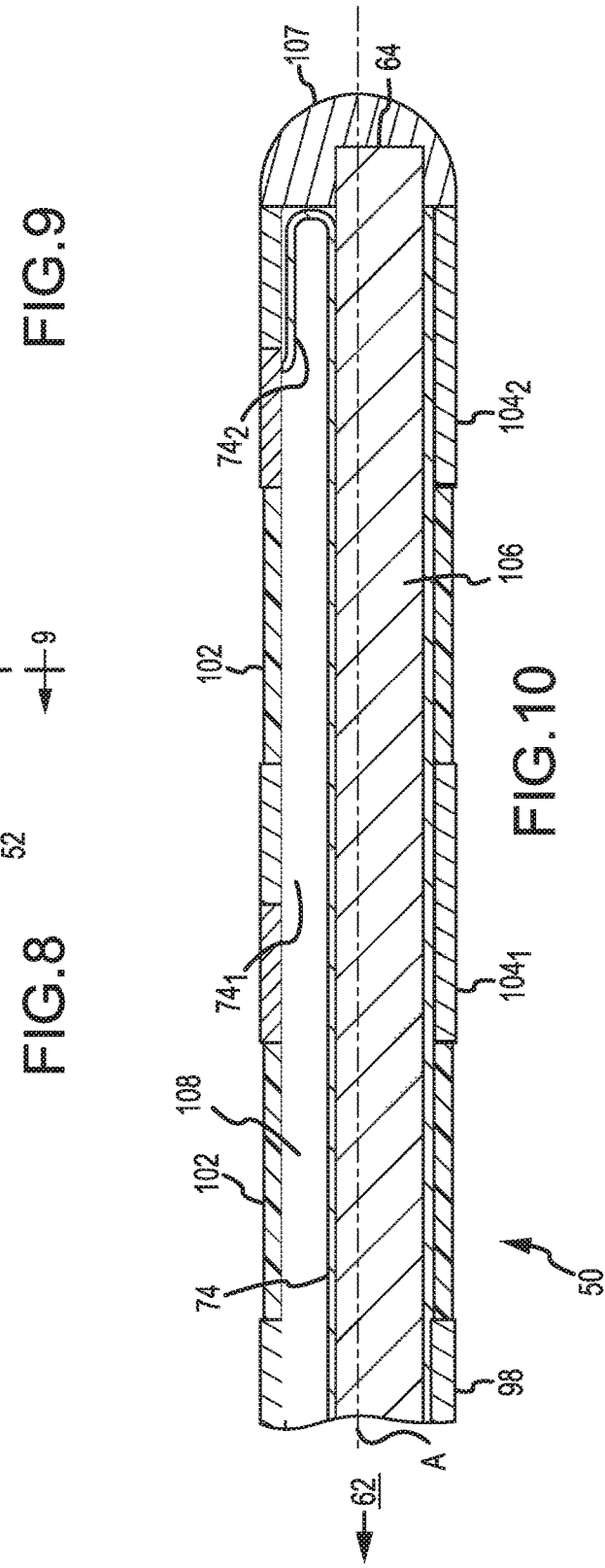

MEDICAL DEVICE GUIDEWIRE WITH HELICAL CUTOUT AND COATING

BACKGROUND OF THE INVENTION a. Field of the Invention

The instant disclosure relates generally to a medical device guidewire, and more specifically to a medical device guidewire with a position sensor.

b. Background Art

Various diagnostic and therapeutic procedures in or on the body of a patient, such as in the circulatory system, the gastrointestinal tract, the brain vessels, the bronchial tree or the like may be performed or facilitated by inserting a catheter into a body lumen and thereafter navigating the diagnostic or therapeutic catheter to the target anatomical site. To facilitate navigation of the catheter, a guidewire is often used. The guidewire typically has a reduced diameter relative to the catheter; the reduced diameter aids a physician in inserting and navigating the guidewire to the anatomical site. The catheter is then passed over the guidewire and guided to the target site.

One method for maneuvering a guidewire involves the use of fluoroscopy to track the position of a guidewire, particularly its distal tip, during navigation. Another method of maneuvering a guidewire to an operational site is to place one or more position sensors on the guidewire, track the sensors with a navigation system, and display a real-time or rendered image of the guidewire for the clinician manipulating the guidewire to view. One such system for maneuvering a guidewire is detailed in U.S. application Ser. No. 12/357,971 filed 22 Jan. 2009 (published as U.S. patent application publication no. 2009/0192412 A1 on 30 Jul. 2009), which is hereby incorporated by reference as though fully set forth herein.

Repeated contact between the tip of the guidewire and anatomical features of the patient during navigation is inevitable. Such contact can place unwanted stress on the structure of the guidewire and potentially damage the guidewire. To reduce instances of contact while maneuvering a guidewire to a target anatomical region, it is desirable for a clinician to be able to "see" the extreme distal tip of the guidewire. Accordingly, in embodiments where the guidewire is tracked by a navigation and positioning system, it is desirable to place a position sensor as close to the distal tip of the guidewire as possible. Moreover, regardless of the location of the position sensors on the guidewire, it is also desirable to protect the position sensor(s) and associated wiring from bending-induced stress as well as from exposure to body fluids to ensure reliable electrical function of the sensors. In addition, in the situation where the guidewire is used in delivering a cardiac pacing lead, it would be desirable that the guidewire be configured to be mechanically and electrically compatible with the lead.

The foregoing discussion is intended only to illustrate the present field and should not be taken as a disavowal of claim scope.

BRIEF SUMMARY OF THE INVENTION

In an embodiment, a guidewire may comprise an elongate body, a proximal connector assembly, a corewire, and a sensor assembly. The elongate body comprises a proximal and distal end portions. The body further has an annular wall that defines an interior lumen. The proximal connector assembly may be coupled to the proximal end portion of the body. The proximal connector assembly may be configured for connection to a medical positioning system. The corewire may have proximal and distal end portions. The corewire may extend through the lumen of the elongate body. The sensor assembly may be located on the distal end portion of the corewire and distal of the elongate body. The sensor assembly may be electrically connected by a pair of electrical conductors to the proximal connector assembly. The sensor assembly may be configured to generate an electrical signal indicative of at least a position of the sensor assembly in a reference coordinate system defined by the medical positioning system. The annular wall of the elongate body may include a helical cutout extending over a predetermined length of the distal end portion of the elongate body. The helical cutout may be configured to increase the flexibility of the elongate body over the predetermined length of the distal end portion of the body.

In an embodiment, a guidewire may comprise an elongate body, a proximal connector assembly, a corewire, a sensor assembly, and an outer coating. The elongate body comprises proximal and distal end portions. The body further has an annular wall that defines an interior lumen. The proximal connector assembly may be coupled to the proximal end portion of the body. The proximal connector assembly may be configured for connection to a medical positioning system. The corewire may have proximal and distal end portions. The corewire may extend through the lumen of the elongate body. The sensor assembly may be located on the distal end portion of the corewire and distal of the elongate body. The sensor assembly may be electrically connected by a pair of electrical conductors to the proximal connector assembly. The sensor assembly may be configured to generate an electrical signal indicative of at least a position of the sensor assembly in a reference coordinate system defined in the medical positioning system. The outer coating may be radially-outwardly of at least the sensor assembly and may comprise an elastomer material. The outer coating may be configured to surround the distal end portion of the corewire and the sensor assembly. The coating may have a substantially continuous outer surface with a substantially uniform outside diameter along an axial length thereof.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 4 is a cross-sectional side view of a portion of the guidewire of FIG. 3.

FIG. 5 is a cross-sectional side view of a portion of the guidewire of FIG. 3.

FIG. 6 is a cross-sectional side view of a portion of the guidewire of FIG. 3.

FIG. 7 is a diagrammatic side view of a portion of a body of the guidewire of FIG. 3, illustrating a helical cutout on the body.

FIG. 8 is a cross-sectional side view of a portion of the guidewire of FIG. 3.

FIG. 9 is a circumferential cross-sectional view of the guidewire of FIG. 8, taking substantially along line 9-9.

FIG. 10 is a cross-sectional side view of a portion of the guidewire of FIG. 3.

DETAILED DESCRIPTION OF THE INVENTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Figure 1:
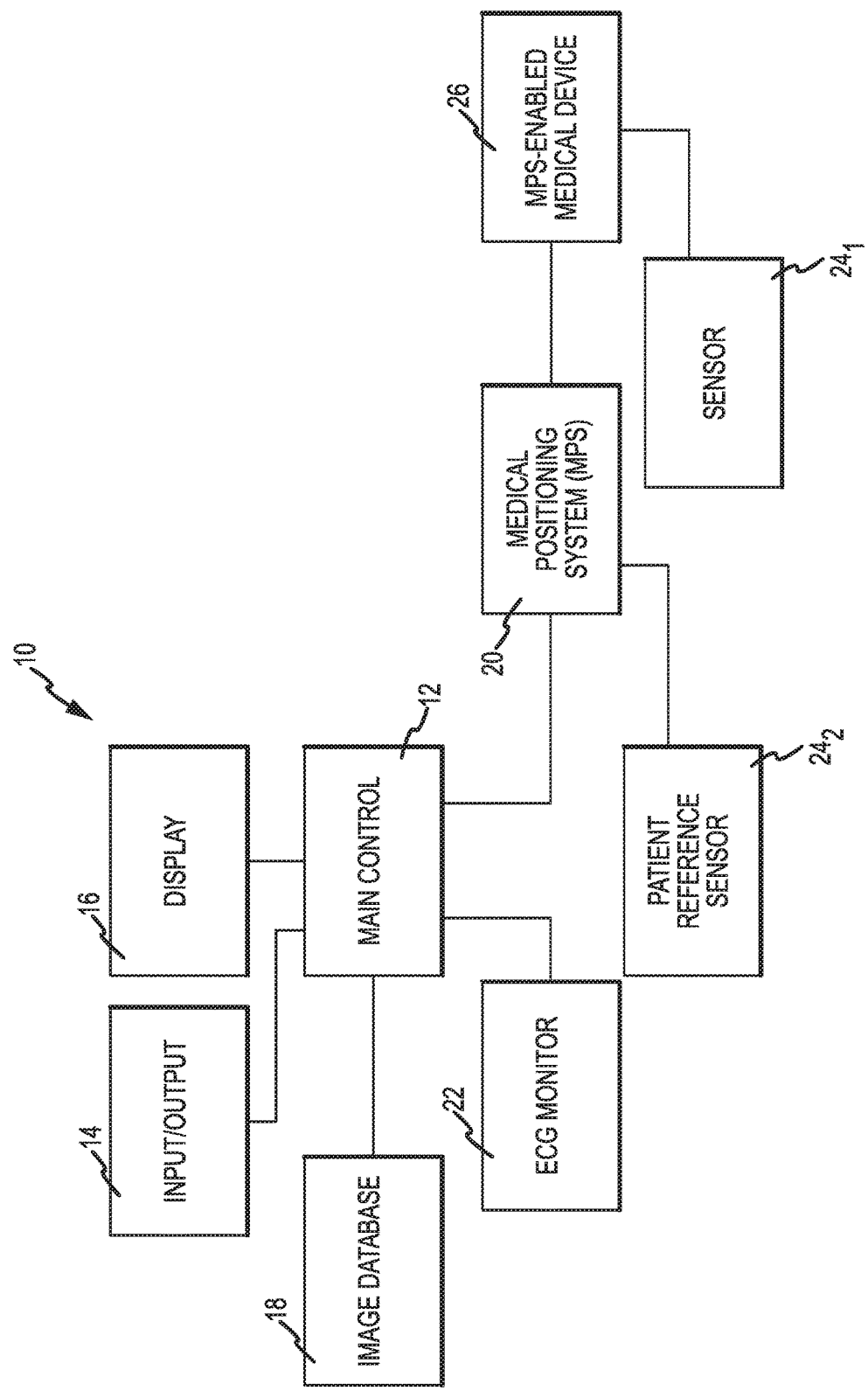
FIG. 1 is a schematic and block diagram view of a system incorporating an embodiment of a guidewire.

Referring now to the drawings wherein like reference numerals are used to identify identical or similar components in the various views, FIG. 1 is a block diagram view of a system 10 in which a position sensing guidewire may be used. System 10 as depicted includes a main electronic control unit 12 (e.g., including one or more electronic processors) having various input/output mechanisms 14, a display 16, an optional image database 18, a localization system such as a medical positioning system (MPS) 20, an electrocardiogram (ECG) monitor 22, one or more MPS location sensors respectively designated $24_1$ and $24_2$, and an MPS-enabled guidewire 26 which itself includes one and optionally more MPS location sensors, shown in exemplary fashion as having one such sensor $24_1$.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Embodiments consistent with the instant disclosure may find use in navigation applications that use imaging of a region of interest. Therefore system 10 may optionally include image database 18. Image database 18 may be configured to store image information relating to the patient's body, for example, a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database 18 may also include three-dimensional image data as well. It should be further understood that the images may be acquired through any imaging modality, now known or hereafter developed, for example X-ray fluoroscopy, ultra-sound, computerized tomography, nuclear magnetic resonance or the like.

MPS 20 is configured to serve as the localization system and therefore to determine positioning (localization) data with respect to one or more of MPS location sensors $24_i$ (where i=1 to n) and output a respective location reading. The location readings may each include at least one or both of a position and an orientation (P&O) relative to a reference coordinate system, which may be the coordinate system of MPS 20. For example, the P&O may be expressed as a position (i.e., a coordinate in three axes X, Y and Z) and orientation (i.e., an azimuth and elevation) of a magnetic field sensor in a magnetic field relative to a magnetic field generator(s) or transmitter(s).

Figure 2:
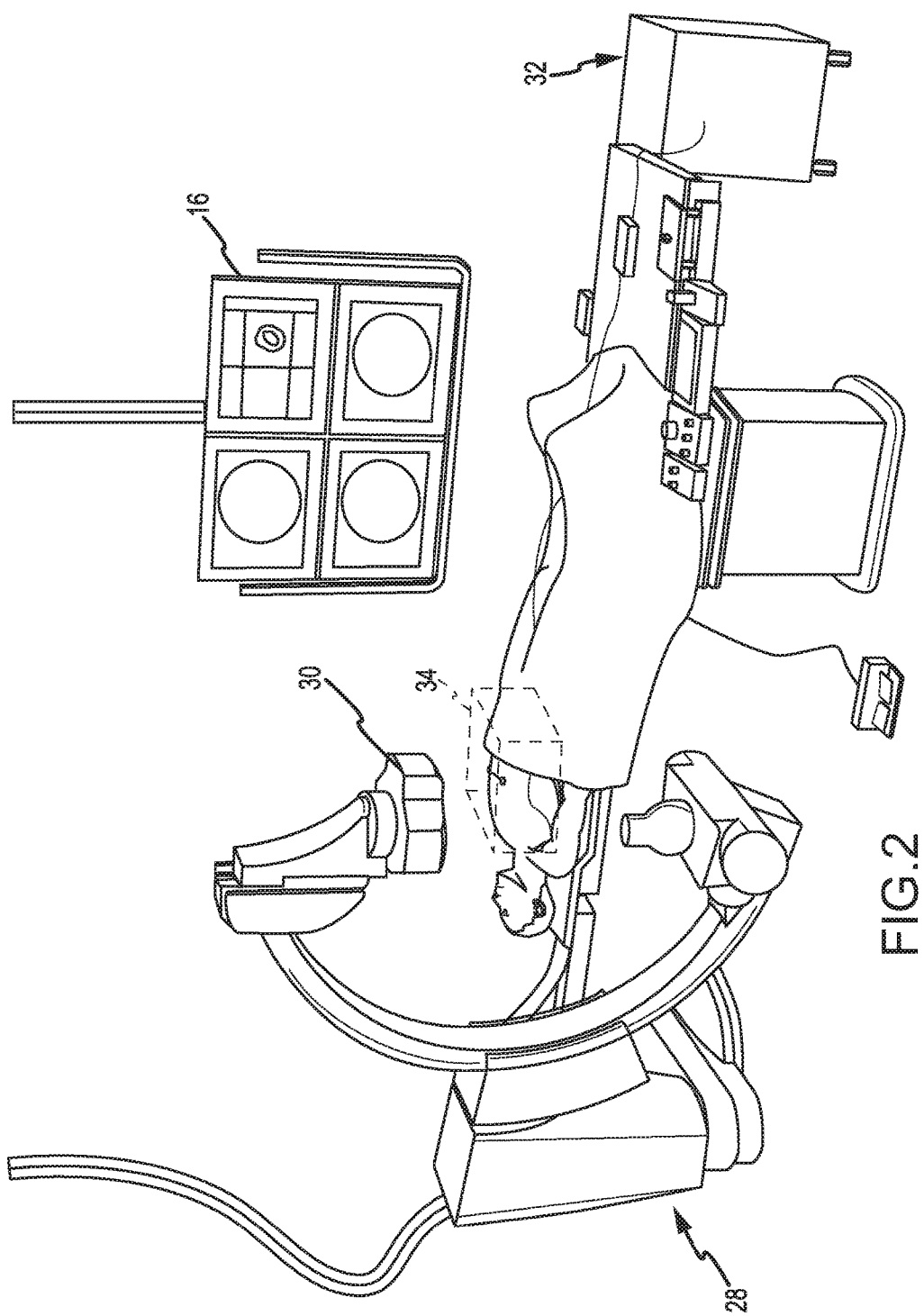
FIG. 2 is a diagrammatic view of an exemplary catheter-lab environment in which the system of FIG. 1, particularly including a medical positioning system (MPS) enabled guidewire, may be used.

MPS 20 determines respective locations (i.e., P&O) in the reference coordinate system based on capturing and processing signals received from the magnetic field sensors $24_i$ while such sensors are disposed in a controlled low-strength AC magnetic field (see FIG. 2). From an electromagnetic perspective, these sensors develop a voltage that is induced on the sensing coil residing in a changing magnetic field, as contemplated here. Sensors $24_i$ are thus configured to detect one or more characteristics of the magnetic field(s) in which they are disposed and generate an indicative signal, which is further processed by MPS 20 to obtain a respective P&O thereof. Exemplary design features and manufacturing processes and methods for sensors $24_i$ and medical devices incorporating such sensors are known in the art.

MPS sensor $24_1$, and optionally additional MPS sensors in further embodiments, may be associated with MPS-enabled medical device 26. Another MPS sensor, namely, patient reference sensor (PRS) $24_2$ (if provided in system 10) is configured to provide a positional reference of the patient's body so as to allow motion compensation for gross patient body movements and/or respiration-induced movements. PRS $24_2$ may be attached to the patient's manubrium sternum, a stable place on the chest, or another location that is relatively positionally stable. Like MPS location sensor $24_1$, PRS $24_2$ is configured to detect one or more characteristics of the magnetic field in which it is disposed wherein MPS 20 provides a location reading (e.g., a P&O reading) indicative of the PRS's position and orientation in the reference coordinate system.

The electro-cardiogram (ECG) monitor 22 is configured to continuously detect an electrical timing signal of the heart organ ("organ timing signal") through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized play-back of a previously captured sequence of images (cine loop) stored in database 18. ECG monitor 22 and ECG-electrodes may both comprise conventional components.

FIG. 2 is a diagrammatic view of system 10 as incorporated into a larger system, namely, a catheter lab. More specifically, the system 10 is shown as being incorporated into an fluoroscopic imaging system 28, which may include commercially available fluoroscopic imaging components. It should be understood that while embodiments may be used in the catheter-lab environment to be described below, this is exemplary only and not limiting in nature. MPS 20 includes a magnetic transmitter assembly (MTA) 30 and a magnetic processing core 32 for determining location (P&O) readings. MTA 30 is configured to generate the magnetic field(s) in and around the patient's chest cavity, in a predefined three-dimensional space identified as a motion box 34. MPS sensors $24_i$ as described above are configured to sense one or more characteristics of the magnetic field(s) and when the sensors are in motion box 34, each generate a respective signal that is provided to magnetic processing core 32. Processing core 32 is responsive to these detected signals and is configured to calculate respective P&O readings for each MPS sensor $24_i$ in motion box 34. Thus, MPS 20 enables real-time tracking of each sensor $24_i$ in three-dimensional space.

The positional relationship between the image coordinate system and the MPS reference coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used. One exemplary embodiment of an MPS 20 will be described in greater detail below in connection with FIG. 13.

Figure 3:
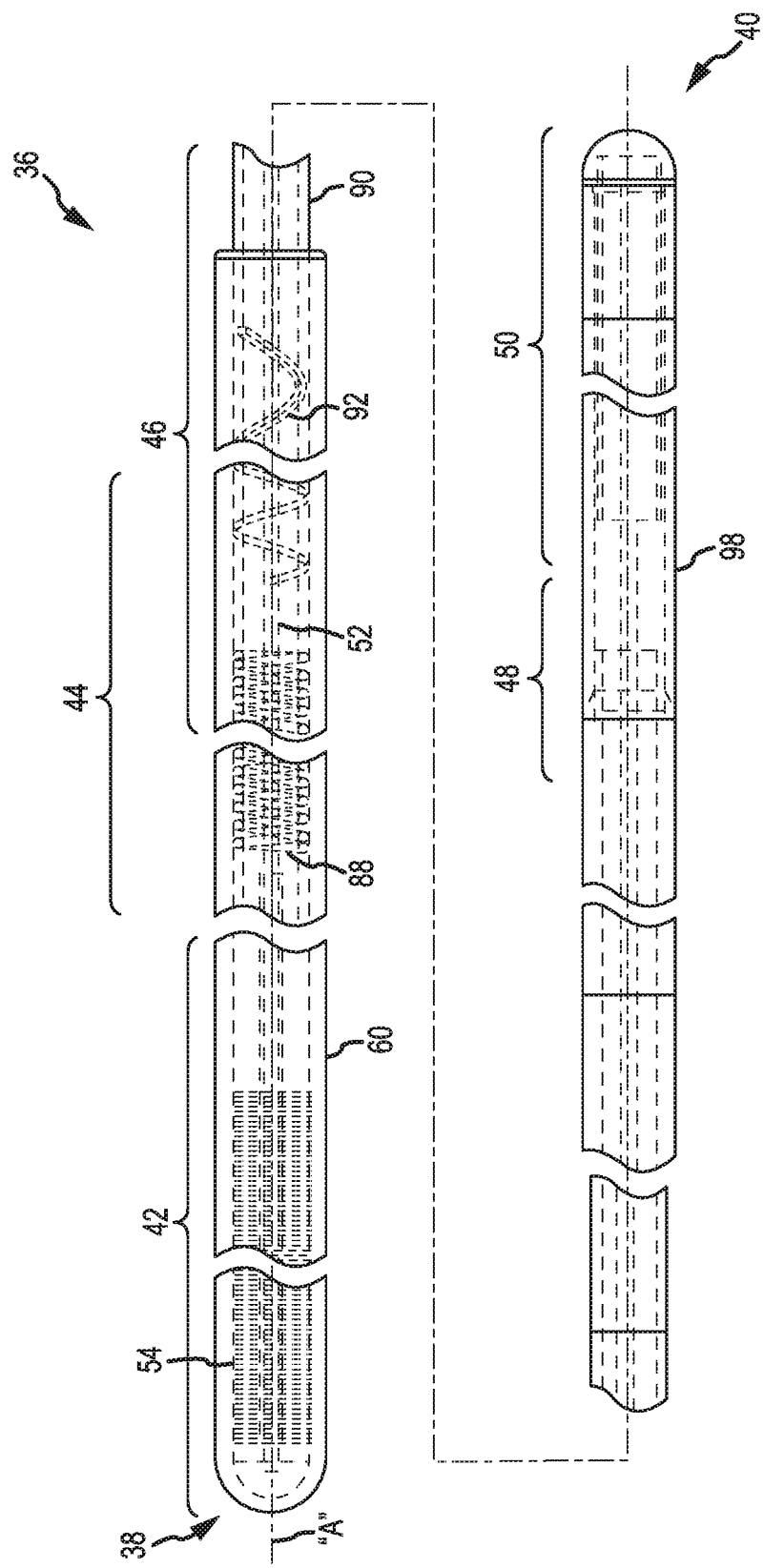
FIG. 3 is a diagrammatic view of an embodiment of a guidewire.

FIG. 3 is a diagrammatic view, with portions broken away, of a guidewire 36 that may be used as the medical device 26 in system 10 (FIG. 1). FIG. 3 shows guidewire 36 in a completed state of assembly and several components thereof will be identified before proceeding to the remainder of the detailed description. Guidewire 36 is generally elongate and extends along a central longitudinal axis designated "A" between a guidewire distal end 38 and a guidewire proximal end 40.

The guidewire 36 includes a sensor assembly 54 (i.e., best shown in FIG. 4) having an output signal useful for position detection. As shown, the sensor assembly 54 is very close the extreme distal end 38, and hence provides very accurate indication of the location of the distal tip, for example, for intra-body navigation.

The guidewire 36 further includes an elastomeric coating 60 (i.e., best shown in FIG. 4) whose uniform outside diameter (OD), smooth outer surface is particularly useful for delivering cardiac pacing leads, which fit over coating 60 without entanglement.

The guidewire 36 further includes a body 90 (e.g., tube, best shown in FIG. 7) having a helical cut out 92 (i.e., best shown in FIG. 7) whose pitch decreases towards distal end 38, thus increasing the flexibility of body 90 towards distal end 38. The increase in flexibility improves navigability.

The proximal end of tube 90 is ground (i.e., reduced outside diameter) so as to permit mechanical coupling to a proximal connector assembly 98. The proximal connector assembly 90 also provides electrical connectivity between the guidewire (i.e., in particular the sensor assembly 54) and external equipment, such as MPS 20.

The guidewire 36 further includes a central corewire 52 (i.e., best shown in FIGS. 4-6 and 8) extending generally from proximal connector assembly 98 to the extreme distal plug of guidewire 36. The corewire 52 provides improved mechanical properties of the guidewire 36. For descriptive purposes only, guidewire 36 may have a first portion 42, a second portion 44, a third portion 46, a fourth portion 48, and a fifth portion 50. Each portion will be described in further detail below.

Figure 12:
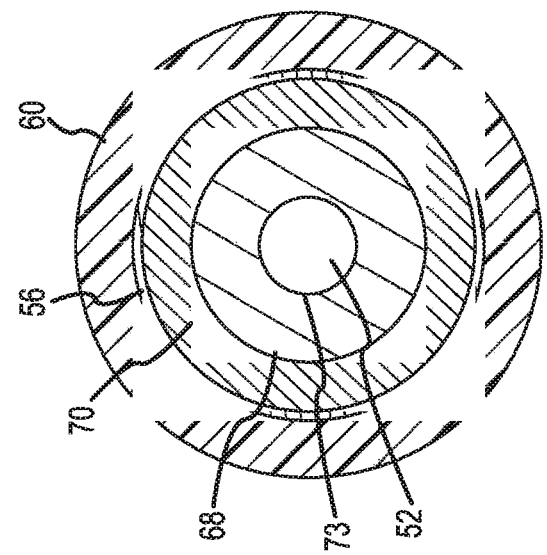
FIG. 12 is a circumferential cross-sectional view of the guidewire of FIG. 4, taking substantially along line 12-12.
Figure 11:
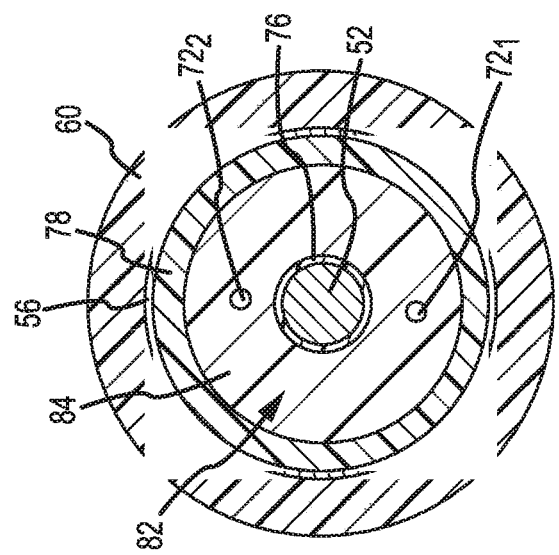
FIG. 11 is a circumferential cross-sectional view of the guidewire of FIG. 4, taking substantially along line 11-11.

FIG. 4 is a diagrammatic, cross-sectional side view showing the distal end of guidewire 36 in greater detail (i.e., first portion 42), with portions broken away. FIGS. 11 and 12 are cross-sectional views taken along lines 11-11 and 12-12, respectively, in FIG. 4. Guidewire 36 includes central corewire 52, sensor assembly 54, a shroud 56, a plug 58, and a coating 60.

Corewire 52 is configured to distribute bending stresses, tensile loads, and compressive loads over its length, reducing stress on the other components of guidewire 36, such as the wiring that electrically connects sensor assembly 54 to the proximal connector assembly 98. In other words, loads (e.g., due to contact with tissue) imposed on shroud 56 are transferred via coating 60 to plug 58 to corewire 52, and similarly loads directly imposed on coating 60 to plug 58 are likewise resolved through corewire 52. Corewire 52 contributes to the overall mechanical properties of the guidewire 36.

Corewire 52 is located substantially at the radial center of guidewire 36. In other words, a central longitudinal axis 66 of corewire 52 is substantially the same as or coincident with central axis "A" of guidewire 36. Corewire 52 has a distal end portion which, in the illustrated embodiment, generally coincides with guidewire distal end 38, and is at least as co-extensive as the axial extent of shroud 56. An extreme distal end 62 of corewire 52 may be flush with or may extend distally a distance $d_1$ past the distal end of the sensor assembly 54, being situated substantially in the central region of plug 58. In distal end portion, corewire 52 has a circular cross-section of constant diameter (best seen in FIGS. 11-12). Corewire 52 further includes a proximal end portion 64, as seen in FIG. 8.

In an embodiment, corewire 52 may be made of metal, such as stainless steel, titanium, or nickel titanium alloys (i.e., NITINOL), or other biocompatible material. In an embodiment, corewire 52 may be a single continuous wire extending substantially the entire axial length of guidewire 36 (i.e., form proximal connector 98 to plug 58), which may provide the benefit of distributing bending stresses over the entire length of guidewire 36. In another embodiment (not shown), corewire 52 may be a multi-piece construction, such as the construction described in U.S. application Ser. No. 12/359,010 filed 23 Jan. 2009 (published as U.S. patent application publication no. 2009/0192413 A1 on 30 Jul. 2009), hereby incorporated by reference as though fully set forth herein.

The illustrated embodiment of corewire 52 is intended to be exemplary only and not limiting. Many variations could be made to corewire 52 and still fall within the spirit and scope of the present disclosure. For example, corewire 52 may comprise a material other than metal and may have a non-circular cross-section. Additionally, corewire 52 may be solid, hollow, or have some other interior construction.

Sensor assembly 54 is configured to detect one or more characteristics of a magnetic field in which it is disposed and produce an output electrical indicative thereof. The output signal, as described above (see description relating to sensor 24) can be processed by MPS 20 to produce a location of the sensor assembly 54. The location can include at least one or both of the position and orientation of the sensor assembly 54 in a reference coordinate system. In an embodiment, sensor assembly 54 may be substantially similar or the same as the sensor assembly described in U.S. application Ser. No. 12/980,848 filed 29 Dec. 2010, hereby incorporated by reference as though fully set forth herein.

Sensor assembly 54 is located radially-outwardly from corewire 52 and may comprise multiple elements, or may be unitary. In the illustrated embodiment, sensor assembly 54 comprises a hollow cylindrical sensor core 68 with a wire 70 wound on sensor core 68 to form a sensor coil with two free ends thereof forming a pair of sensor leads $72_1$, $72_2$ which are available at a proximal end of sensor assembly 54. Sensor core 68 may be a tube comprising magnetically permeable material, with the tube having a central lumen, where corewire 52 passes through the central lumen.

A clearance 73 may exist between an inner diameter of sensor core 68 and outer diameter of corewire 52, as seen in FIG. 11. Clearance 73 may be filled with an insulating material, such as epoxy, which secures sensor core 68 to corewire 52 and insulates sensor core 68 from corewire 52. Sensor core 68 may comprise magnetically-permeable material which increases the overall sensitivity of the sensor core/sensor coil combination 68, 70 that forms positioning sensor assembly 54 (as compared to the same coil configuration without a magnetically-permeable core). In an embodiment, sensor core 68 may be made of a metal alloy of magnetically-permeable material, such as an alloy of nickel and iron.

In an embodiment, when sensor core 68 is secured (e.g., via epoxy) to the distal end portion of corewire 52, corewire 52 may additionally act as a safety wire. In the event that any portion of guidewire 36 is structurally compromised (e.g., body 90 is fractured), the bond between corewire 52 and sensor assembly 54 maintains the structural integrity with the extreme distal end portion 62 of guidewire 36. The bond between corewire 52 and sensor assembly 54 acts as a safety feature allowing for extraction of the extreme distal end of guidewire 36 from the patient. In an embodiment, corewire 52 may additionally be secured to the proximal end of guidewire 36, such as bonding proximal end portion 64 of corewire 52 to proximal connector assembly 98 using an adhesive 108 (e.g. epoxy), and the safety feature of corewire 52 may be maintained from distal end to proximal end of guidewire 36.

As described above, a function of sensor assembly 54, in the context of a magnetic field based positioning system, is to detect one or more characteristics of the magnetic field(s) in which sensor assembly 54 is placed. In this regard, one of ordinary skill in the art will appreciate there are many variations and configurations of sensor assembly 54. For example and without limitation, while sensor assembly 54 is shown in the distal end portion of guidewire 36, the position of sensor assembly 54 and/or position of a plurality of sensor assemblies 54 may be located throughout guidewire 36 and such variations and configurations remain within the spirit and scope of the present disclosure.

With continued reference to FIG. 4, guidewire 36 may further comprise a wire cable 74, an insulator tube 76, and an alignment tube 78. Wire cable 74 may comprise a first wire $74_1$ and a second wire $74_2$. First wire $74_1$ and second wire $74_2$ may be twisted together, forming a twisted pair along a substantial length of wire cable 74. For example, for the substantial portion of the axial length of guidewire 36, starting from proximal connector assembly 98 and extending distally towards sensor assembly 54, the wires $74_1$, $74_2$, remain twisted, as shown in FIG. 5. The twisting of the wires improves noise reduction, as known. However, as the wire cable 74 approaches sensor assembly 54, the two wires $74_1$, $74_2$ are separated (i.e., untwisted) in order to allow respective electrical connection to the two free ends of sensor coil 70.

In this regard, sensor leads $72_1$, $72_2$ are conductively connected to wire cable 74 at connection nodes $80_1$, $80_2$. As shown, sensor lead $72_1$ may be conductively connected (i.e., electrically connected) to first wire $74_1$ at connection node $80_1$, and sensor lead $72_2$ may be conductively connected to second wire $74_2$ at connection node $80_2$.

Insulator tube 76 is configured to electrically isolate corewire 52 from the other electrically active components at the distal end of guidewire 36. In this regard, sensor leads $72_1$, $72_2$, connection nodes $80_1$, $80_2$, and a portion of wire cable 74 are electrically insulated from corewire 52 by insulator tube 76. In an embodiment, insulator tube 76 may be a polymer tube, such as, but not limited to, polyimide, that is slipped onto corewire 52. Alternatively, insulator tube 76 may comprise a heat-activated "shrink" tube comprising electrically insulting material. In a further embodiment, insulator tube 76 may be a layer of polymer that is sprayed onto or otherwise applied to corewire 52, or some other electrically insulating structure on corewire 52.

Alignment tube 78 is configured to provide mechanical protection for the sensor assembly/twisted pair connections (i.e., connections $80_1$, $80_2$), particularly from externally-imposed forces encountered during use (e.g., contacting body/tissue structures). One failure mode for a guidewire of the type including such electrical connections is the disconnection or failure of the electrical connection at one or both of $80_1$, $80_2$. The alignment tube 78 helps mitigate this problem. In addition, alignment tube 78 is configured to provide a uniform outside diameter structure onto which shroud 56 can conform. Alignment tube 78 thus also provides a manufacturing function.

The alignment tube 78 is located proximal of the sensor assembly 54 and distal of a body coil 88. Alignment tube 78 may have an outside diameter that is approximately the same as the outside diameter of the sensor assembly 54, and have an inside diameter that is large enough to enclose at least the connections $80_1$, $80_2$ that the tube 78 is configured to protect. Alignment tube 78 may comprise a polymer tube comprising, for example only, polyimide material or the like.

Referring to FIG. 12, alignment tube 78 includes an interior space, designated space 82 that is large enough to accommodate sensor leads $72_1$, $72_2$, connection nodes $80_1$, $80_2$, and a portion of wire cable 74, which are routed therethrough. In an embodiment, space 82 may ultimately be filled with a nonconductive epoxy material 84. Epoxy material 84, when cured, provides mechanical protection for sensor leads $72_1$, $72_2$, connection nodes $80_1$, $80_2$, and a portion of wire cable 74. Epoxy material 84 also bonds insulator tube 76, sensor leads $72_1$, $72_2$, connection nodes $80_1$, $80_2$, a portion of wire cable 74, sensor core 68, sensor coil 70, a portion of shroud 56, a portion of corewire 52, and body coil 88 together.

Referring to FIGS. 4-5 and FIGS. 11-12, shroud 56 is configured to provide a smooth, substantially continuous cylindrical sub-assembly to which the corewire 52 can be bonded (i.e., provides a potting volume). In addition, shroud 56 may provide some measure of protection to the interior components of the distal assembly from compressive and tensile loads resulting from insertion, removal, and bending of guidewire 36. The shroud 56 comprises a tube that directly covers the outer circumferential surfaces of sensor assembly 54, alignment tube 78, and a portion of epoxy material 84. A distal end of shroud 56 may be aligned with the distal end of sensor assembly 54 and the distal end of shroud 56 may be adjacent to a proximal end of plug 58. Shroud 56 may be a polymer shrink tube or another electrically insulating structure or material. For example only, shroud 56 may comprise polyethylene terephthalate (PET) material, although shroud 56 may comprise materials other than PET. The illustrated embodiment of shroud 56 is exemplary only, and should not be construed as limiting. Although shroud 56 is shown as a thin-walled tube of substantially constant diameter, shroud 56 may have another shape or cross-section, which may be constant or may vary along its axial length.

Plug 58 is provided at the extreme distal end of guidewire 36 for structural support and to provide for non-traumatic contact of the extreme distal end of guidewire 36 when introducing and navigating the guidewire through a lumen of a patient. Plug 58 is preferably rounded and may be made of polymer, glue, bonding material, metal, or any other relatively smooth material suitable for this purpose. Plug 58 is shown in a hemispherical shape, but may be in any other non-traumatic form. Plug 58 may be coupled to one or more of corewire 52, sensor assembly 54, and shroud 56 by gluing, bonding, welding, soldering, or another patient-safe coupling method.

FIGS. 5-6 and 8 are cross-sectional side views, with portions broken-away, of second portion 42, third portion 44, fourth portion 46 of guidewire 36. FIG. 7 is a diagrammatic side view of a body 90 having a helical cutout 92. As seen in FIGS. 5-8, guidewire 36 may further comprise body coil 88, body 90, and helical cutout 92.

Body coil 88 is configured to provide bending flexibility as well as, in an embodiment, radiopacity by virtue of material selection. In this regard, body coil 88 may comprise radiopaque material (e.g., metal), such as platinum, to increase fluoroscopic visibility. Body coil 88 may also be made of stainless steel, iridium, or nickel titanium alloys (i.e., NITINOL). In addition to providing flexibility and fluoroscopic visibility, body coil 88 also protects cable wiring 74 that is proximally located with respect to shroud 56. The proximal end of body coil 88 may be soldered to tube 90 while the distal end of body coil 88 may be bonded to sensor assembly 54 by conventional methods (e.g., with an adhesive such as medical grade epoxy, or with another patient-safe (biocompatible) coupling method).

Body 90, which may comprise a flexible elongate hollow tube that allows the passage of electrical wiring therethrough. Body 90 thus includes an annular wall 94 defining a central lumen 96 configured to provide sufficient space for the electrical wiring as well as the corewire 52, while at the same time having a minimum impact on the torque transfer and structural characteristics of the guidewire 36. As described above, corewire 52 and cable wiring 74 run throughout lumen 96.

As best shown in FIG. 8, the proximal end of body 90 is attached to proximal connector assembly 98. The proximal end of body 90 may be ground down (i.e., reduced outside diameter), for example as a taper or as a step or shoulder, to facilitate attachment to connector assembly 98. As shown in FIG. 8, the reduced outside diameter of body 90 corresponds to the inside diameter of the distal end portion of proximal connector body 98, thereby allowing a low-clearance fit or interference fit.

As best shown in FIG. 3, body 90 may have variable outside diameter along various portions of body 90. For example, in an embodiment, the outside diameter of the distal portion of body 90 may be smaller than the outside diameter of the proximal portion of body 90. This difference in outside diameter may be seen by comparison of the two distal-most tube portions in FIG. 3 (i.e., the proximal portion of tube 90 has a greater outside diameter than the adjacent distal portion). The reduced outside diameter along the distal portion of body 90 provides radial space for coating 60 without the resultant outside diameter exceeding a preferred maximum outside diameter of guidewire 36.

In an embodiment, the progressively decreasing outside diameter of body 90 (as taken in the distal direction) may be achieved by reducing the thickness of annular wall 94 by known methods. For example, one known method may involve grinding down or drawing down the outer surface of annular wall 94. Through the foregoing, the inside diameter of body 90 remains the same, but the thickness of annular wall 94 along the distal portion of body 90 is reduced, thereby also reducing the outside diameter thereof. In an embodiment, the reduced thickness of annular wall 94 may extend approximately ten inches from the distal end of body 90 toward the proximal end of body 90. The reduction in thickness of annular wall 94 may be performed in steps, or may be a gradual transition. The reduced thickness of the body may be used to design a preferred amount of flexibility of body 90. In an embodiment, body 90 may be made of metal. When body 90 is metal, it may be connected to an electrical ground and act as electrical interference shielding for wire cable 74 passing through lumen 96 of body 90.

Body 90 is provided with a helical cutout 92 to configure body 90 with greater or lesser levels of flexible in predefined areas. Helical cutout 92, in an embodiment, involves completely removing wall material from annular wall 94. In an embodiment, helical cutout 92 may extend substantially from the distal end of body 90 for a predetermined axial length, spiraling proximally towards the proximal end of body 90. In one embodiment, the pitch, which may be defined as the axial distance corresponding to one revolution of the helix, is substantially constant. In another embodiment, however, the pitch varies as a function of axial position from the distal end of body 90.

Referring to FIG. 7, body 90 is provided with helical cutout 92 that has a progressively increasing pitch as the helical cutout 92 extends away from the distal end of body 90 toward the proximal end of body 90. For example, in a first interval $100_1$ (distal-most portion of body 90) no helical cutout 92 is provided on body 90. In second, third, fourth, fifth, sixth and seventh intervals $100_2$-$100_7$, respectively, the pitch along body 90 (axially) either increases or is maintained. An eighth interval $100_8$ of body 90 does not incorporate a helical cutout 92. The lower the pitch, the more flexible body 90 will be in that interval. In the illustrated embodiment, body 90 will be most flexible along distal end and gradually become less flexible (e.g., more stiff) as helical cutout 92 moves proximally. In an embodiment, the pitch of helical cutout 92 may transition gradually. In an embodiment, helical cutout 92 may have a width "W" as seen in FIG. 6. In an embodiment, width "W" of helical cutout 92 may be substantially constant. In an embodiment, the tube 90 may be hypo tube stock, and where the helical cutout 92 may be formed using laser cutting or other methods known in the art. Although one embodiment of width "W" of helical cutout 92 has been provided, it is appreciated that other widths may be used to control the amount of flexibility as desired, and other widths not provided in detail remain within the spirit and scope of the present disclosure.

Coating 60 creates a smooth, continuous, substantially uniform outside diameter surface which is advantageous in some medical applications, such as delivering pace-maker leads and other implantable device leads. For example, the nature of the outer surface of coating 60 acts as a lubricant of sorts with an inside diameter of such leads, preventing lock up of the inside diameter surface of the leads with the outside diameter surface of sensor assembly 54 and body coil 88. Coating 60 is a radially outermost hyperelastic polymeric layer disposed on distal portion of guidewire 36. Coating 60 may be a relatively soft and flexible material, such as a polyurethane elastomer commercially available under the trade designation PELLETHANE, from The Lubrizol Corporation, Wickliffe, Ohio, USA. In a PELLETHANE material embodiment, the material used for coating 60 may have a hardness of about 55 D (durometer). In another embodiment, the material used for coating 60 may have a hardness range of about 35 D to 65 D. It should be understood, however, that other materials may be used for coating 60, such as an thermoplastic elastomer available under the trade designation SANTOPRENE available from ExxonMobil Chemical Company, Houston, Tex., USA.

Coating 60 completely circumferentially surrounds plug 58 and extends proximally over body 90 to approximately the point where the taper of body 90 begins. Thus, coating surrounds shroud 56, body coil 88, helical cutout 92 and a portion of body 90. Coating 60 completely covers helical cutout 92, and therefore seals what would otherwise be an opening into body 90 caused by helical cutout 92. Coating 60 advantageously seals the distal end portion of guidewire 36, rendering the distal end portion of guidewire 36 watertight. Coating 60 may be hydrophilic or hydrophobic, and may have an overcoat of hydrophilic coating material. In an embodiment, the maximum outermost diameter of coating 60 does not exceed a maximum outermost diameter at any point along the entire guidewire 36. In an embodiment, coating 60 may have a thickness such that a maximum outer diameter of the guidewire 36 may be 0.0140 inches to 0.0145 inches. This may be advantageous in allowing a pacing lead to pass over the entire length of guidewire 36.

FIGS. 9-10 are cross-sectional views of an embodiment of fifth portion 50 of guidewire 36. FIG. 9 is a circumferential cross-sectional view of proximal connector assembly 98. FIG. 10 is a diagrammatic cross-sectional side view of proximal connector assembly 98.

In an embodiment, proximal connector assembly 98 may be substantially similar to a connector assembly described in U.S. Pat. No. 8,109,889, hereby incorporated by reference as though fully set forth herein. Connector assembly 98 is a bending resistant male-type connector disposed on the proximal end of guidewire 36 configured to conductively engage a female-type connector that is operatively connected to medical positioning system 20. Electric signals from sensor assembly 54 are communicated to the MPS 20 for determining a location reading of the sensor assembly 54, as described above.

In an embodiment, connector assembly 98 may comprise a plurality of insulator sleeves 102, a plurality of conductor rings 104, and a D-shaped pin 106. D-shaped pin 106 is positioned in a lumen of connector assembly 98, as shown in FIG. 9. A distal end of D-shaped pin 106 is attached to proximal end of corewire 52 using adhesive 108 (e.g., epoxy). A proximal end of D-shaped pin 106 is attached to a proximal tip 107. D-shaped pin 106 may provide additional structure to connector assembly 98 as well as clearance for wire cable pass through the lumen of connector assembly 98. A first wire $74_1$ of wire cable 74 is conductively connected to a first conductor ring $104_1$. A second wire $74_2$ of wire cable 74 is conductively connected to a second conductor ring $104_2$. The distal end of connector assembly 98 is attached to a reduced diameter of the proximal end portion of body 90. Insulator sleeves 102 are positioned adjacent to conductor rings 104. The lumen of connector assembly 98 may be filled with an insulating material, such as epoxy, which may secure D-shaped pin 106, wire cable 74, insulator sleeves 102, and conductor rings 104 to connector assembly 98. The insulating material may also provide additional rigidity for connector assembly 98.

A method of manufacturing an embodiment of guidewire 36 will now be set forth. Body coil 88 is soldered to the distal end of body 90. Next, insulator tube 76 is placed onto corewire 52 (distal end) and then trimmed to length. Corewire 52 is bonded to sensor assembly 54 (e.g., using epoxy). The larger alignment tube 78 is then slid on over corewire 52 and cable 74. Once the leads 72 from sensor assembly 54 have been soldered to the distal end leads from wiring 74, then alignment tube 78 is slid into place over solder joints 80. Shroud 56 (e.g., shrink tube) is then placed over sensor assembly 54 and alignment tube 78. Epoxy is introduced into cavity 73 (i.e., interior of the shrink tube), using known means (e.g., a needle). Heat is applied, which shrinks shrink tube 56 to the outside diameter of sensor assembly 54 and alignment tube 78, but also cures the epoxy. An additional dab of epoxy is applied to the distal end of guidewire 36, including corewire 52, thereby forming hemispherical plug 84. From the proximal end of body 90 of guidewire 36, wiring 74 (twisted pair) is pulled through for alignment at the proximal end. Body 90 is slid distally and body 90 (i.e., the distal portion of body coil 88) is adhered (e.g., epoxy) to sensor assembly 54 (see detail FIG. 5). The electrical connections between wiring 74 and proximal connector assembly 98 are made. Corewire 52 is also bonded to proximal connector assembly 98. The coating 60 is applied.

Figure 13:
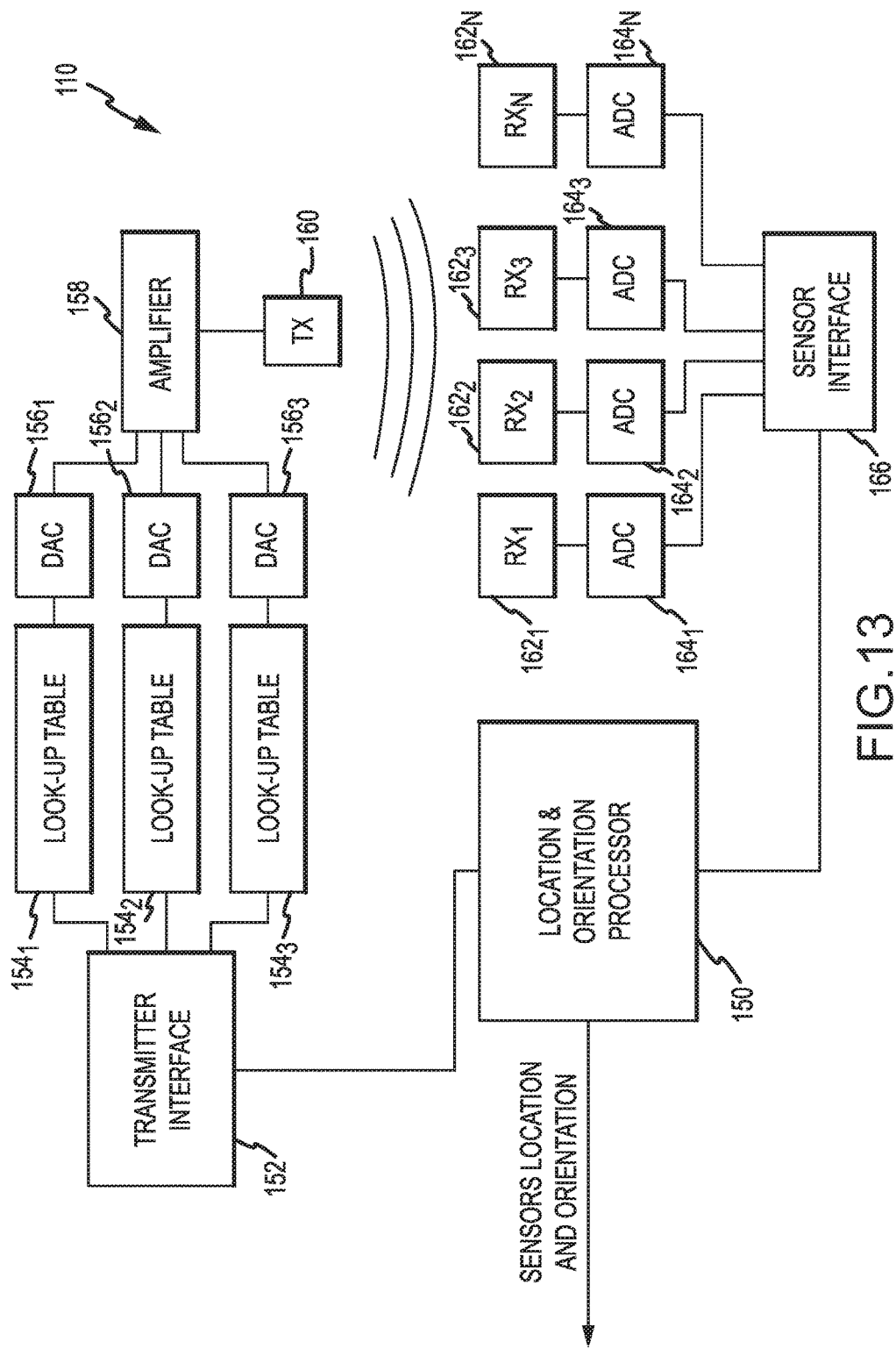
FIG. 13 is a schematic and block diagram view of one exemplary embodiment of a medical positioning system (MPS) as shown in block form in FIG. 1.

FIG. 13 is a schematic and block diagram of one exemplary embodiment of MPS 20, designated as a MPS 110, as also seen by reference to U.S. Pat. No. 7,386,339, referred to above, and portions of which are reproduced below, which generally describes, at least in part, the MediGuide™ Technology system commercially offered by MediGuide Ltd. of Haifa, Israel and now owned by St. Jude Medical, Inc. It should be understood that variations are possible, for example, as also seen by reference to U.S. Pat. No. 6,233,476, hereby incorporated by reference as though fully set forth herein. Another exemplary magnetic field-based MPS is the Carto™ system commercially available from Biosense Webster, and as generally shown and described in, for example, U.S. Pat. Nos. 6,498,944, and 6,788,967, both hereby incorporated by reference as though fully set forth herein. Accordingly, the following description is exemplary only and not limiting in nature.

MPS 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly the main electronic control unit 12, as described above may include conventional processing apparatus known in the art, capable of executing pre-programmed instructions stored in an associated memory, all performing in accordance with the functionality described herein. Such an electronic control unit may further be of the type having both ROM, RAM, a combination of non-volatile and volatile (modifiable) memory so that any software may be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A guidewire comprising:
   an elongate body formed from a tube including a proximal portion and a distal portion, the elongate body further including an annular wall that defines an interior lumen;
   a proximal connector assembly connected to the proximal portion of the elongate body, the proximal connector assembly being configured for connection to a medical positioning system;
   a corewire including a proximal portion and a distal portion, the corewire extending through the interior lumen;
   a sensor assembly located on the distal portion of the corewire and distal of the elongate body, the sensor assembly being electrically connected by a pair of electrical conductors to the proximal connector assembly;
   an electrically insulating structure that surrounds the corewire and insulates the corewire from the pair of electrical conductors;
   a D-shaped pin including a proximal portion and distal portion, wherein the distal portion of the D-shaped pin is connected to the proximal portion of the corewire and the proximal portion of the D-shaped pin is connected to a proximal portion of the proximal connector assembly; and a pair of longitudinally extending electrical conductors disposed between a flattened surface of the D-shaped geometrically configured pin and an inner surface of the proximal connector.

2. The guidewire of claim 1, wherein the insulating structure that surrounds the corewire is a tube.

3. The guidewire of claim 1, wherein the insulating structure that surrounds the corewire comprises a heat shrink material.

4. The guidewire of claim 1, wherein the insulating structure that surrounds the corewire comprises a coating.

5. The guidewire of claim 1, wherein the electrically insulating structure electrically isolates the corewire from the pair of electrical conductors.

6. The guidewire of claim 1, further comprising:
a plug coupled with the distal portion of the corewire, wherein the plug has a distal, non-traumatic tip portion.

7. The guidewire of claim 1, wherein the sensor assembly and the pair of electrical conductors are electrically connected at a pair of connection nodes, further including:
an alignment tube proximal of the sensor assembly configured in size to enclose the pair of connection nodes, to thereby protect the pair of connection nodes from external forces.

8. The guidewire of claim 7, wherein the electrically insulating structure electrically isolates the corewire from the pair of connection nodes.

* * * * *